United States Patent [19]

Ilardi et al.

[11] Patent Number: 5,481,031

[45] Date of Patent: Jan. 2, 1996

[54] PROCESS FOR PREPARING NARROW RANGE ALKOXYLATED ISETHIONATES

[75] Inventors: Leonora Ilardi, Englewood; Christine Wenzel, Ridgewood, both of N.J.

[73] Assignee: Lever Brothers Company, Division of Conopco, Inc., New York, N.Y.

[21] Appl. No.: 325,857

[22] Filed: Oct. 19, 1994

Related U.S. Application Data

[63] Continuation-in-part of Ser. No. 54,660, Apr. 23, 1993, abandoned.

[51] Int. Cl.⁶ .................. C07C 309/10; C07C 303/02
[52] U.S. Cl. .................................. 562/110; 562/111
[58] Field of Search .......................... 562/110, 111

[56] References Cited

U.S. PATENT DOCUMENTS 3,823,185  7/1974  Schlossman ............... 260/513 B

*Primary Examiner*—Peter O'Sullivan
*Attorney, Agent, or Firm*—Ronald A. Koatz

[57] ABSTRACT

The present invention relates to a process for preparing narrow range alkoxylated isethionates while reducing amounts of undesirable product using water levels and stir rates unappreciated in the art.

22 Claims, No Drawings

PROCESS FOR PREPARING NARROW RANGE ALKOXYLATED ISETHIONATES

RELATED APPLICATIONS

The present application is a Continuation-in-Part of U.S. Ser. No. 08/054,660, filed Apr. 23, 1993, now abandoned.

BACKGROUND OF THE INVENTION

1. Field of the Invention

The present invention relates to a process for preparing narrow range alkoxylated isethionates. The narrow range alkoxylated isethionates are desirable in that they may be further processed to produce fatty acid esters of alkoxylated isethionates such as are disclosed in applicants' copending application, U.S. Ser. No. 08/045,951, filed Apr. 12, 1993. The invention relates to alkoxylated isethionate (or non-alkoxylated isethionates) prepared by said process.

2. Background of the Invention

The production of fatty acid esters of alkoxylated isethionates is disclosed in U.S. Ser. No. 08/045,951 filed Apr. 12, 1993, now allowed, and hereby incorporated by reference into the subject application.

In U.S. Ser. No. 08/045,951, alkoxylated isethionate are made either (1) by the sulfonation of corresponding chloroalkoxy alcohol or (2) by reaction of alkylene oxide and sodium isethionate or bisulfite. With regard to the second method, there is no teaching of a specific method of making a narrow range alkoxylated isethionate, let alone of a method of making it in a simple batch process. With regard to the first method, the method of the present invention is advantageous in that (1) it is cheaper (e.g., no need to buy chloroethoxy ethanol as starting reagent); (2) it is easier to process; and (3) there is some monomer distribution, which may be more desirable than having no distribution at all.

U.S. Pat. No. 2,810,747 to Sexton et al. teaches a method of producing a sodium isethionate substantially free of sodium sulfate, sodium sulfite, and other impurities. The patent is further concerned with minimizing formation of glycol and glycol ether (including glycol ether of isethionate, i.e., alkoxylated isethionates). Thus, not only does the references discourage formation of alkoxylated isethionate, but further there is clearly no teaching or suggestion of a method of producing and optimizing the formulation of alkoxylated isethionates within a narrowed alkylene oxide range.

U.S. Pat. No. 3,823,185 to Schlossman does teach a process for preparation of alkoxylated isethionates. However, this reaction involves a distilling step in which all or part of the water present in the reaction mixture is removed after a small amount of ethylene oxide has been reacted. In the only example shown, 98.7% water is removed. The reference clearly suggests that water increases polyether by-products and that use of large amounts of water should be avoided. Further, the reference neither teaches nor suggests a method of preparing an alkoxylated isethionate having not only a narrow distribution of alkylene oxide units, but also a narrow distribution having a low alkylene oxide content. Finally, there is no recognition that both temperature and stir rate must be kept below certain critical levels in order to achieve decreased levels of undesirable by-product. All of this in direct contrast to the process of the present invention where increased amounts of water (i.e., at least 10% water should be used according to the present invention) have been found to (1) increase reaction rate (2) increase narrow range alkylene oxide distribution and (3) not simultaneously increase undesirable by-product.

Further, as noted above, Schlossman does not teach or suggest the criticality of both low temperature (i.e., below about 95° C.) and low stirring (i.e., below about 100 rpm, preferably about 50 rpm) to ensure that a narrow distribution of low alkylene oxide product is formed while minimizing undesirable by-products (e.g., glycols).

U.S. Pat. No. 3,029,264 to Alphen et al. teaches a process for the preparation of fatty acyl oxyalkylene sulphonates in which HOR'SO$_3$M is used as a starting reactant. There is no teaching at all, however, of how this starting reactant is made.

An object of this invention is to find a process for production of alkoxylated isethionate and narrow range distribution of alkylene oxide units.

A further object of the invention is to find a process for doing so while minimizing formation of undesirable by-products, e.g., glycols.

A further object of the invention is to provide a process which accomplishes the aforementioned goals without use of a catalyst and which can be accomplished in a simple, batch-like process in optimal reaction times.

SUMMARY OF THE INVENTION

The present invention provides a process for producing alkoxylated isethionate:

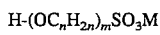

$$H\text{-}(OC_nH_{2n})_m SO_3M$$

wherein n= 2 to 4, the yield of product where m is 2 (e.g., monoethoxy isethionate) is at least about 28% by weight of total reaction product, preferably about 28% to about 55% of total reaction product; M is hydrogen, an alkali metal such as lithium, sodium or potassium, an alkaline earth metal such as calcium, magnesium or strontium, ammonium, alkyl ammonium wherein the alkyl group is preferably a straight chain group having 1 to 22 carbons, alkanolamine, a cationic amino acid such as arginine or other salt forming cation such as, for example, a substituted pyridinium; and wherein the process comprises reacting about 2 to 5 mols alkylene oxide, preferably 3–4 moles alkylene oxide per mole bisulfite (or per mole isethionate) and at least 10% by weight water in a reaction batch.

The process of the invention must be conducted at relatively low temperatures (below about 95° C., preferably below about 90° C., more preferably about 25° C to about 89° C.) and at relatively low stirring (i.e., below about 100 rpm, more preferably below about 50 rpm) to ensure that a narrow distribution of low alkylene oxide product is formed at substantially reduced by-product (e.g., glycols) levels.

The invention is further concerned with a process for preparing narrow range alkoxylated isethionate having the formula:

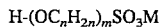

$$H\text{-}(OC_nH_{2n})_m SO_3M$$

wherein n=2 to 4 and the yield of the product where m equals 2 to 3 (e.g., monoethoxy isethionate SEI and diethoxy isethionate SDI) is at least about 32% by weight of total reaction product, preferably about 32% to about 75% by weight; and M is as defined above.

The process is run in the absence of catalysts although, of course, catalysts may be added if desired.

DETAILED DESCRIPTION OF THE INVENTION

The present invention is concerned with a process for preparing narrow range alkoxylated isethionates having the formula below:

$$H\text{-}(OC_nH_{2n})_mSO_3M$$

wherein n=2 to 4, the yield of product where m equals 2 (e.g., monoethoxy isethionate, SEI) is at least 28% by weight of total reaction product, preferably about 28% to about 55% by weight; and M is hydrogen, an alkali metal such as lithium, sodium or potassium, an alkaline earth metal such as calcium, magnesium or strontium, ammonium, alkyl ammonium wherein the alkyl group is preferably a straight chain group having 1 to 22 carbons, alkanolamine, a cationic amino acid such as arginine or other salt forming cation such as, for example, a substituted pyridinium.

The invention is further concerned with a process for preparing narrow range alkoxylated isethionate having the formula $$H\text{-}(OC_nH_{2n})_mSO_3M$$

wherein n=2 to 4, and the yield of product where m equals 2 and 3 (e.g., monoethoxy isethionate SEI and diethoxy isethionate SDI) is at least 32% by weight of the total reaction product, preferably about 32% to about 75% by weight; and M is as defined above.

By narrow range distribution alkoxylate is meant that at least 28% and up to as high as about 56% by weight of reaction product has m of 2 (e.g., is monoalkoxylated) or at least 32% and up to as high as about 75% by weight of reaction product has m of 2 to 3 (i.e., is mono- or diethoxylated as defined above). As described in greater detail below, the percent of reaction product having a narrow range distribution is increased as the weight percent of water used in the reaction is increased. That is, the weight percent distribution of monoalkoxylated or mono plus dialkoxylated product can be pushed into the higher ranges defined above by using more water in the initial reaction.

The formation of such narrow range alkoxylate distribution is important because the product can then be further reacted to produce fatty acid esters of narrow range distribution alkoxylated isethionates such as those described in U.S. Ser. No. 08/045,951, filed Apr. 12, 1993.

The process for preparing the narrow range alkoxylated isethionates is a simple batch process which need not involve additional catalysts.

The process involves reacting alkylene oxide, bisulfite (for example, potassium or sodium bisulfite), and water in an autoclave or other reactor at specified temperatures, pressures, reaction times, and stirring rates as described below. Alternatively, the reaction involves reacting alkylene oxide, isethionate (for example, potassium or sodium isethionate) at specified temperatures, pressures, reaction times, and stirring rates.

The alkylene oxide can be any alkylene oxide wherein the alkyl group has 2 to 10 carbons, preferably 2 to 5 carbons, but 2 carbons (i.e., ethylene oxide) or 3 carbons (propylene oxide) are most preferred.

If bisulfite is used, the bisulfite can be any commercially available bisulfite source. If isethionate is used, this too can be commercially available isethionate.

M is hydrogen; an alkali metal such as lithium, sodium or potassium; an alkaline earth metal such as calcium, magnesium or strontium; ammonium; alkyl ammonium wherein the alkyl group is preferably a straight chain group having 1 to 22 carbons; alkanolamine; a cationic amino acid such as arginine; or other salt forming cation such as, for example, a substituted pyridinium.

A surprising aspect of the invention was the levels of water used and the consequences water amounts had both on reaction rates and alkoxylate distribution, while the level of undesirable by-products (e.g., polyethylene glycol) was minimized.

Thus, for example, while levels of as little as 6–10% water by weight were used, as the weight percent of water was raised, reaction times were drastically reduced. At 100° C., for example reaction time decreased from 94 hours (at 11% water) to 1.25 hours (at 55% water). Further, the percentage of alkoxylated isethionate (i.e., monoalkoxylated product SEI and dialkoxylated product SDI where m=2 and 3) increased from about 45% to about 53%. Even at 20% by weight water, percentage of alkoxylated isethionate (m=2 and 3) went from 45% to 60%. Only at levels of 75% by weight water did the amount of mono-and dialkoxylated product go slightly down.

While the rate production of mono- and dialkoxylated product (i.e., SEI and SDI isethionate) did not increase with water content at all temperatures (e.g., at 75° C., production went from about 72% (20% water) to about 56% (55% water), a pattern of greater alkoxylation when lower amounts of water were used was evident. At 25° C., while only isethionate (m=1) was present at 33% water, both isethionate and alkoxylated isethionate (e.g., m=2 and 3) were present at 55% water.

In addition to water content, the production of alkoxylated isethionate is dependent on reaction temperature, reaction pressure and stirring rates as defined below.

The temperature may vary from 20° to about 95° C., preferably 25° to below about 90° C. Most preferably, temperatures are run at from about 30° to 89° C.

Reaction time may vary from minutes (depending on water amount and temperature) to days or weeks. Preferably, reaction times vary from about 45 minutes to 24 hours, more preferably 45 minutes to 7 hours.

In a preferred embodiment of the invention the water level used is greater than about 33%, preferably 33% to 75% by weight, more preferably 33% to about 70% of the total reaction mixture and the temperature is from about 80° to 90° C.

Pressure varies from 20 to 200 psi, preferably 40 to 160 psi.

Another criticality of the invention is the stirring rate. It is not sufficient that the temperature be below about 95° C., but the stirring rate must also be low enough to prevent significant formation of by-products such as glycols. The stir rate must be below about 100 rpm, preferably about 50 rpm.

While not wishing to be bound by theory, it is believed that the low stir rate and temperature result in a reaction slow enough to significantly reduce formation of glycols. For example, when mixing was done in a narrow 45 ml autoclave, this is believed to have resulted in slow mixing of mainly the bottom portion of the sample while, when moved to a larger 100 ml autoclave, calculated stir rates had to be lowered to below about 100 rpm to achieve the same results.

The number of mols alkylene oxide used varies from about 2 to 5, preferably 2 to 3 per mole bisulfite (or per mole isethionate). The number of moles is at least partially dependent on the temperature and amount of water used. For example, if the temperature of the reaction is at about room temperature (e.g., about 25° C.), to drive a reaction producing the defined amounts of product, greater than 2 moles may be required and/or greater amounts of water (e.g., at 2 EO greater than 50% $H_2O$ is required) are needed. Stated differently, if only 2 moles EO are used, temperature should be at least about 35° C. and, if 3 moles EO are used at lower temperatures water concentration should be greater than 50%. While not wishing to be bound by theory, it is believed that a greater mol percentage would lower the percentage of 1-and 2-AO by pushing m to 3, 4 or higher.

Also, as noted above, the reaction requires no catalyst.

While the preferred product of the invention is where m is 2 or 3, it should be readily understood that the process may be used to prepare product where m is 4 or greater.

The present invention is further illustrated by the following examples which are not intended to be limiting any way.

As can be seen from the table above, increasing levels of water generally decreased reaction time (or increased reaction rate) and, at least at 100° C. and 25° C., clearly also increased production of alkoxylated isethionate (m=2 or 3). Further, increased production and reaction times were not at the expense of undesirable PEG product.

EXAMPLES 21–25 2:1 EO:NaHSO₃ Reaction: No catalyst

In these example, ethylene oxide (EO) was combined with sodium bisulfite in a 2:1 EO:NaHSO₃ ratio together with water and were placed in an autoclave under conditions described below:

| EXAM. | REACT.* TEMP. | INITIAL REACT. PRESS. | % H$_2$O IN RXN | REACT. TIME | M = 1 % SI | M = 2 % SEI | M = 3 % SDI | M = 4 or more % SNI | % PEG |
|---|---|---|---|---|---|---|---|---|---|
| 21 | 100° C. | 70 psig | 55 | 45 hrs. | 41.9 | 36.1 | 6.58 | — | 10.5 |
| 22 | 75° C. | 63 psig | 55 | 1¾ hrs. | 50.2 | 27.8 | 3.7 | — | 9.9 |
| 23 | 50° C. | 21 psig | 55 | 18 hrs. | 38.3 | 41.4 | 7.4 | — | 8.6 |
| 24 | 35° C. | — | 55 | 26 hrs. | 57.8 | 33.2 | 4.2 | — | 3.2 |
| 25 | 25° C. | 11 psig | 55 | 18.5 hrs. | 86.9 | 5.2 | — | — | 0.2 |

*Again, temperatures of actual reaction was at least 5°–10° C. below those recited.

EXAMPLES 1–20

Ethylene oxide, sodium bisulfite and water were placed in a 45 milliliter autoclave at the reaction temperatures, water levels and pressure levels set forth below (ratio of ethylene oxide to bisulfite being 3 to 1 ) and the reaction time, percentage isethionate (SI), percentages alkoxylated isethionate (SEl= monoalkoxylated isethionate; SDI=dialkoxylated isethionate where m equals 3; Snl= greater than diethoxylated isethionate where m is greater than or equal to 4) and percentage polyethylene glycol were recorded (calculated in the absence of water) and also set forth below. It should be noted that, although stir rates were not measured in the 45 ml autoclave (because of the viscosity of the solution and the narrow autoclave), stir rates are believed to have been well below the about 100 rpm of the claimed invention.

These examples show that the reaction also works at lower ratios of alkylene oxide to bisulfite. In addition, the reaction advantageously lowered levels of polyethylene glycol by-product although the distribution of alkoxylated isethionate (m= 2 and 3) was slightly lowered.

EXAMPLES 26–27: 2:1 Ratio of EO: Isethionate Reaction: No Catalyst

In this example alkylene oxide was combined with isethionate in 2:1 EO: isethionate ratio with water and placed in autoclave at condition described below:

| EXAM. | REACT.* TEMP. | INITIAL REACT. PRESS. | % H$_2$O IN RXN | REACT. TIME | M = 1 % SI | M = 2 % SEI | M = 3 % SDI | M = 4 or more % SNI | % PEG |
|---|---|---|---|---|---|---|---|---|---|
| 1 | 100° C. | 150 psig | 11 | 94 hrs. | 28.65 | 30.52 | 15.08 | 2.57 | 23.16 |
| 2 | | 160 psig | 20 | 15 hrs. | 17.38 | 34.21 | 26.20 | 1.79 | 20.41 |
| 3 | | 125 psig | 33 | 2.5 hrs. | 18.05 | 36.96 | 23.78 | 0.13 | 19.91 |
| 4 | | 90–100 psig | 47 | 2.0 hrs. | 22.47 | 40.94 | 16.37 | — | 20.20 |
| 5 | | 70–80 psig | 55 | 1.25 hrs. | 26.66 | 40.69 | 12.41 | — | 20.22 |
| 6 | | 70–80 psig | 75 | 50 min. | 35.1 | 39.2 | 5.7 | — | 17.3 |
| 7 | 75° C. | 80 psig | 20 | 19 hrs. | 13.90 | 37.22 | 35.23 | 3.57 | 12.7 |
| 8 | | 70 psig | 33 | 7 hrs. | 16.41 | 40.79 | 26.07 | 0.15 | 16.5 |
| 9 | | 60 psig | 55 | 1.5 hrs | 24.42 | 43.31 | 13.3 | — | 18.9 |
| 10 | | 20 psig | 75 | 70 min | 43.8 | 29.9 | 4.5 | — | 27.8 |
| 11 | 50° C. | 50 psig | 33 | 23 hrs. | 14.80 | 44.12 | 26.91 | 0.16 | 14.01 |
| 12 | | 40 psig | 47 | 21 hrs. | 13.94 | 46.65 | 23.79 | — | 15.61 |
| 13 | | 40 psig | 55 | 6 hrs. | 24.4 | 43.3 | 13.36 | — | 18.6 |
| 14 | | | 75 | 70 min. | 41.3 | 28.2 | 4.2 | — | 26.3 |
| 15 | 35° C. | | 33 | 72 hrs. | 16.2 | 31.7 | 34.8 | — | 12.2 |
| 16 | | | 55 | 48 hrs. | 12.1 | 49.5 | 23.3 | — | 13.7 |
| 17 | 25° C. | 20 psig | 33 | 120 hrs. | 89.3 | — | — | — | 1.61 |
| 18 | | 0 psig | 55 | 21.5 hrs. | 65.44 | 30.10 | 2.09 | — | 2.3 |
| 19 | | 0 psig | 55 | 120 hrs. | 15.10 | 52.30 | 20.30 | — | 13.3 |
| 20 | | 0 psig | 55 | 96 hrs. | 28.8 | 49.8 | 9.8 | — | 9.4 |

*The temperature in the 45 ml autoclave was provided by oil bath and actual reaction temperatures are at least 5°–10° below what is measured. Thus, reaction temperature in the autoclave is always below about 95° C.

| Exam | Substrate | REACT* TEMP | INITIAL REACT PRESS | % H₂O IN RXN | REACT TIME | M = 1 % SI | M = 2 % SEI | M = 3 % SDI | M = 4 or more % SNI | % PEG |
|---|---|---|---|---|---|---|---|---|---|---|
| 26 | Sodium Isethionate | 100° C. | 62 psig | 33 | 3.5 hrs. | 22.0 | 38.2 | 19.3 | — | 20.8 |
| 27 | Potas. Isethionate | 100° C. | 72 psig | 33 | 2.5 hrs. | 21.8 | 36.1 | 20.9 | — | 18.4 |

*Again, temperatures of actual reaction was at least 5°–10° C. below those recited.

This example shows that isethionate can be used as well as bisulfite as a starting reactant for the process of the invention.

EXAMPLE 28

The example of the procedure is set forth below:

A complete description of this preparation is as follows:

In a 45 mL Parr autoclave equipped with a magnetic stir bar, a standard Gage Block assembly (consisting of a nitrogen inlet which doubles as a pressure release valve) and a pressure gauge was placed 3.5g (0.0336 equi.) of sodium bisulfite (ex. Fisher) and 10 mL of distilled deionized water. The mixture was chilled to 5° C. using an ice bath. To this was added 4.5g (0.102 equi.) of condensed ethylene oxide liquid (ex. AGL) delivered from a 0.5 lb. lecture bottle. The block assembly was secured atop the reactor and sealed carefully. At this point, no pressure was registering on the gauge. The mixture was stirred and heated by placing it in an oil bath atop a temperature controlled hot plate stirrer. The mixture was heated until the oil bath reached 100° C. (actual reaction temperature slightly lower). The pressure gauge now read about 70–80 psig. The reaction was allowed to proceed until the pressure gauge read 0 (zero) psig, indicating complete uptake of EO. This occurred after about one hour. After this time, the vessel was opened and the reaction mixture was sparged with nitrogen to remove any traces of EO. The resulting solution was analyzed by HPLC to contain about 55% H₂O, 11.55% SI, 17.73% SEI, 5.4% SDI, and 8.8% PEGs. Titration of the sample revealed 0.002% Na₂SO₃, and 1.43% Na₂SO₄.

EXAMPLES 29–38

In order to show the stirring criticality, applicants measured alkoxylation values and glycol values based on various reactions conducted in 100 ml autoclaves where stirring values and actual reaction temperatures could be measured. Specifically, the reactions measured formation of PEGs in sulfitation of ethylene oxide. All reactions dissolved 10.5 g sodium bisulfite (0.101 mol) in 30 g of dd water. The solution was chilled to 0° C. for the ethylene oxide addition. 14.2 g (0.32 mol) was added to all the reactions except for two where an excess of 16 g (0.36 mol) was used. The reactions were then stirred and heated accordingly.

TABLE

Analysis of Sulfiltration Reactions

| Reaction Temp. | EO Reaction No. | Stir rate (rpm) | % SI | % SMI | % SDI | % PEGs | % Total | Normalized PEGs |
|---|---|---|---|---|---|---|---|---|
| 100° C. | 29 | 450 | 11.41 | 15.155 | 4.925 | 13.62 | 45.11 | 30.19 |
| 100° C. | 30 | 450 | 11.315 | 14.86 | 4.485 | 13.90 | 44.56 | 31.19 |
| 100° C. | 31 | 200 | 11.61 | 15.315 | 4.72 | 14.84 | 46.485 | 31.92 |
| 100° C. | 32 | 200 | 12.11 | 15.08 | 4.27 | 14.15 | 45.61 | 31.02 |
| 86° C. | 33 | 200 | 10.445 | 16.47 | 5.325 | 14.24 | 46.48 | 30.64 |
| 86° C. | 34 | 200 | 10.945 | 15.66 | 4.86 | 12.86 | 44.325 | 29.01 |
| 100° C. | 35 xs EO | 450 | 9.55 | 14.935 | 5.585 | 13.42 | 43.49 | 30.86 |
| 100° C. | 36 xs EO | 450 | 9.37 | 15.22 | 5.96 | 13.85 | 44.40 | 31.19 |
| 86° C. | 37 | ~50 | 10.965 | 16.315 | 5.45 | 12.07 | 44.8 | 26.94 |
| 86° C. | 38 | ~50 | 11.035 | 15.37 | 4.965 | 11.75 | 43.12 | 27.25 |

As can be seen from the Table, the only reactions where PEG levels decreased were those where stir rate was below about 100 rpm, preferably about 50 rpm (i.e., normalized PEG values of 26.94 and 27.25 in reaction numbers 37 and 38). This is consistent with previous work done in narrower 45 ml autoclaves, where it is believed stir rates were also below about 100 rpm and PEG levels were always under 30%.

"Normalized" PEG levels assume that the balance in the reaction mixture is water and is derived by dividing the percent PEG by the total percentage of PEG and alkoxylated isethionate combined.

EXAMPLE 39

Applicants ran a typical reaction in a 100 ml autoclave (as in examples 29–38) at a temperature of 100° C. and at stir rates somewhere between 450 and 500 rpm. Results were as follows:

| Reaction Temp. | Stir rate (rpm) | % SI | % SMI | % SDI | % PEG | % Total |
|---|---|---|---|---|---|---|
| 100° C. | 450–500 | 10.14 | 15.57 | 5.83 | 17.13 | 48.67 |

When stir rate was kept no higher than 450 rpm, normalized PEG rates went to 30%.

While not within the scope of the invention, this example clearly shows how PEG levels tend to decrease as stir rates come down. This is completely unrecognized by the art.

We claim:

1. A one step process for producing alkoxylated isethionate:

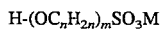

wherein n is 2 to 4; the yield of product where m equals 2 is at least about 28% by weight of the total product; M is selected from the group consisting of hydrogen, alkali metals, an alkaline earth metal, ammonium alkyl ammonium wherein the alkyl group is a straight chain group having 1 to 22 carbons, alkanolamine, a cationic amino acid and salt forming cations; and wherein the process comprises:

reacting bisulfite, an average 2 to 5 mols alkylene oxide per mol bisulfite and at least 10% by weight water in a reaction batch wherein the temperature ranges from about 20° C. to about 95° C., the pressure is 0 to 150 psig and the stir rate is about 50 rpm.

2. A process according to claim 1 wherein m equals 2 is about 28% to about 55% by weight of total product.

3. A process according to claim 1 wherein the bisulfite, alkylene oxide and water are reacted at a temperature ranging from about 20° C. to about 90° C.

4. A process according to claim 3, wherein the temperature is about 35° C. to about 90° C.

5. A process according to claim 3, wherein the temperature is from about 50° C. to 90° C.

6. A process according to claim 1, wherein the pressure is 60 to 150 psig.

7. A process according to claim 1, wherein the alkali metal is selected from the group consisting of lithium, sodium and potassium.

8. A process according to claim 1, wherein the alkaline metal is selected from the group consisting of calcium, magnesium and strontium.

9. A one step process for producing alkoxylated isethionate.

wherein n is 2 to 4, the yield of product where m is 2 to 3 is at least about 32% by weight of the total product; M is selected from the group consisting of hydrogen, alkali metals, alkaline earth metals, ammonium, alkyl ammonium wherein the alkyl group is preferably a straight chain group having 1 to 22 carbons, alkanolamine, a cationic amino acid and salt forming cations, and wherein the process comprises:

reacting bisulfite, an average 2 to 5 mols alkylene oxide per mol bisulfite and at least 10% by weight water in a reaction batch wherein the temperature ranges from about 20° C. to about 95° C., the pressure is 0 to 150 psig and the stir rate is about 50 rpm.

10. A process according to claim 9, wherein m equals 2 to 3 is about 32% to about 75% by weight of total product.

11. A process according to claim 9, wherein the bisulfite, alkylene oxide and water are reacted at a temperature ranging from about 20° C. to about 90° C.

12. A process according to claim 9, wherein the temperature is from about 35° C. to 90° C.

13. A process according to claim 10, wherein the temperature is from about 50° C. to 90° C.

14. A process according to claim 9, wherein the pressure is 60 to 150 psig.

15. A process according to claim 9, wherein the alkali metal is selected from the group consisting of lithium, sodium and potassium.

16. A process according to claim 9, wherein the alkaline earth metal is selected from the group consisting of calcium, magnesium and strontium.

17. An alkoxylated isethionate or mixture of alkoxylated and non-alkoxylated isethionates prepared by the process of claim 1.

18. An alkoxylated isethionate or mixture of alkoxylated and non-alkoxylated isethionates prepared by the process of claim 9.

19. A one step process for producing alkoxylated isethionate:

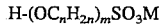

wherein n is 2 to 4; the yield of product where m equals 2 is at least about 36% by weight of the total product; M is selected from the group consisting of hydrogen, alkali metals, an alkaline earth metal, ammonium, alkyl ammonium wherein the alkyl group is a straight chain group having 1 to 22 carbons, alkanolamine, a cationic amino acid and salt forming cations; and wherein the process comprises:

reacting isethionate, an average 2 to 5 tools alkylene oxide per mole isethionate and at least 10% by weight water in a reaction batch wherein the temperature ranges from about 20° C. to about 95° C., the pressure is 0 to 150 psig and the stir rate is about 50 rpm.

20. An alkoxylated isethionate or mixture of alkoxylated and non-alkoxylated isethionate prepared by the process of claim 19.

21. A one step process for producing alkoxylated isethionate

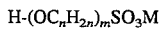

wherein n is 2 to 4; the yield of product wherein M equals 2 or 3 is at least about 57% by weight of the total product; M is selected from the group consisting of hydrogen, alkali metals, an alkaline earth metal, ammonium, alkyl ammonium wherein the alkyl group is a straight chain group having 1 to 22 carbons, alkanolamine, a cationic amino acid and salt forming cations; and wherein the process comprises:

reacting isethionate, an average 2 to 5 mols alkylene oxide per mole isethionate and at least 10% by weight water in a reaction batch wherein the temperature ranges from about 20° C. to about 95° C., the pressure is 0 to 150 psig and the stir rate is about 50 rpm.

22. An alkoxylated isethionate or mixture of alkoxylated and non-alkoxylated isethionate prepared by the process of claim 21.

* * * * *